United States Patent [19]
Fleischer et al.

[11] 3,943,181
[45] Mar. 9, 1976

[54] SEPARATING OPTICALLY PURE d- AND l-ISOMERS OF MENTHOL, NEOMENTHOL AND ISOMENTHOL

[75] Inventors: Jürgen Fleischer, Cologne; Kurt Bauer; Ruldolf Hopp, both of Holzminden, all of Germany

[73] Assignee: Haarmann & Reimer Gesellschaft mit beschrankter Haftung

[22] Filed: Sept. 3, 1974

[21] Appl. No.: 503,004

Related U.S. Application Data
[63] Continuation of Ser. No. 229,109, Feb. 24, 1972, abandoned.

[30] Foreign Application Priority Data
Feb. 27, 1971 Germany............................. 2109456
Feb. 2, 1972 Germany............................. 2204771

[52] U.S. Cl...... 260/631 R; 260/473 R; 260/471 R; 260/468 R; 260/476 R
[51] Int. Cl.²......................................... C07C 35/12
[58] Field of Search..................... 260/631 R, 631 H

[56] References Cited
UNITED STATES PATENTS
2,120,131  6/1938  Harris............................ 260/631 H
FOREIGN PATENTS OR APPLICATIONS
568,085  1/1933  Germany........................ 260/631 H
397,212  8/1933  United Kingdom............. 260/631 R OTHER PUBLICATIONS
Gilman Ed., Organic Chemistry, Wiley, N.Y., 1943, p. 254.
Reed et al., J. Chem. Soc., pp. 167–173 (1933).

*Primary Examiner*—Bernard Helfin
*Assistant Examiner*—James H. Reamer
*Attorney, Agent, or Firm*—Burgess, Dinklage & Sprung

[57] ABSTRACT

A process for the separation of optically active d- and l-isomers of a compound selected from the group consisting of menthol, neomenthol and isomenthol, which comprises esterifying a d,l-isomeric mixture of the compound with an acid selected from the group consisting of benzoic acid optionally carrying at least one substituent on the benzene ring and hexahydrobenzoic acid; forming a supersaturated solution or a supercooled melt of the d,l-ester; inoculating the solution or melt with crystals of the d- or l-form of the ester to effect selective crystallization of one of the two optical isomers; separating the crystals and subjecting them to hydrolysis to yield the corresponding enantiomorph of the starting compound.

5 Claims, 1 Drawing Figure

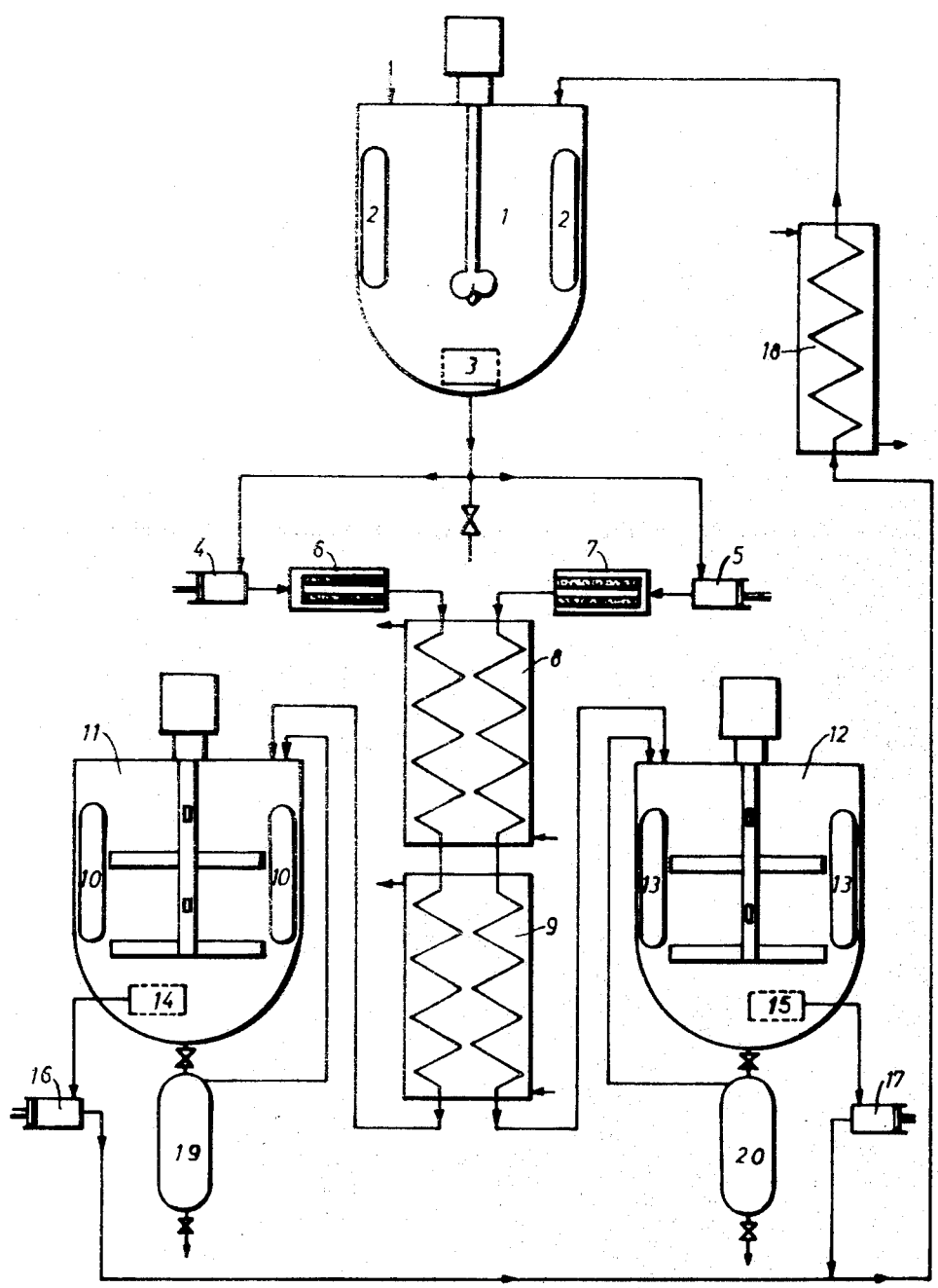

SEPARATING OPTICALLY PURE d- AND l-ISOMERS OF MENTHOL, NEOMENTHOL AND ISOMENTHOL

This is a continuation of application Ser. No. 229,109, filed Feb. 24, 1972, now abandoned.

This application relates to separating optically pure d- and l-isomers of menthol, neomenthol and isomenthol.

Processes for the synthetic production of menthol, neomenthol and isomenthol are known. Unfortunately, the products obtained are mixtures of the d- and l-form and are inferior in their properties to the optically pure isomers. For example, a mixture of d- and l-menthol is distinctly inferior to the l-menthol which occurs naturally in peppermint oil because of the dcontent. Accordingly, there is considerable interest in processes for separating the d- and l-isomers of menthol, neomenthol and isomenthol.

The separation of these optical isomers can be carried out for example by fractional crystallization of the salts of optically active amines such as cinchonine, brucine, strychnine, ephedrine and 1-($\alpha$-naphthyl)-ethyl amine, with d,l-menthyl hydrogen phthalate or hydrogen succinate or the corresponding d,l-neomenthyl derivatives. The separation process as a whole includes formation of a salt with the optically active amine; separation of the two diastereomeric semi ester salts by crystallization; splitting the d- and l-semi ester salt into the optically active esters and finally hydrolyzing these into the d- and l-forms. In addition to the fact that the described process is a multi-stage process which uses optically active bases, which are themselves extremely difficult to prepare, the physiologically harmful bases used during splitting must be very carefully removed in view of the use of l-menthol for example in foodstuffs, confectionary and body-care preparations.

Because of the difficulties mentioned above, naturally occurring starting materials must always be used in the largescale production of optically pure isomers of menthol, neomenthol and isomenthol, for example in the recovery of l-menthol or neomenthol, peppermint oil which contains the l-menthol or d-neomenthol itself, or optically active citronella recovered from oil of citronella may be used. Unfortunately, these natural starting materials fluctuate both in quality and in composition, depending upon their origin. Accordingly, it would constitute a major technical step forward if a synthetically obtained isomer mixture could be used as starting material in the large-scale production of the aforementioned compounds.

It has now been found that the optically active d- and l-isomers of menthol, neomenthol and of isomenthol can be recovered by esterifying the d,l-isomer mixture of the corresponding compound with benzoic acid which optionally contains one or more substituents on the benzene ring, or with hexahydrobenzoic acid; inoculating a supersaturated solution or a supercooled melt of the resulting d,l-ester with crystals of the d- or l-form of the ester and, in this way, selectively crystallizing one of the two optical enantiomorphs, and hydrolyzing the resulting ester of the d- or l-form by methods known per se.

Apart from the esters of benzoic acid or of hexahydrobenzoic acid themselves, the esters of monosubstituted or polysubstituted benzoic acids are also preferably used for the process according to the invention. In such cases the carbocyclic nucleus may contain as substituents: alkoxy groups, preferably lower alkoxy groups containing up to 4 carbon atoms; nitro groups; halogen atoms such as fluorine, chlorine, bromine; or alkyl groups, preferably lower alkyl groups containing up to 4 carbon atoms which may be substituted by halogen atoms, such as trichloromethyl or trifluoromethyl groups.

The d,l-esters of benzoic acid, hexahydrobenzoic acid, 4-methylbenzoic acid, 3,5-dinitrobenzoic acid 4-methoxy-and 4-ethoxybenzoic acid are preferably used for the process according to the invention.

It has proven to be of particular advantage for carrying out the separation by the process according to the invention to use the d,l-ester of benzoic acid, hexahydrobenzoic acid, 4-methylbenzoic acid, 3,5-dinitrobenzoic acid or of 4-ethoxybenzoic acid for menthol, and the d,l-ester of 4-methylbenzoic acid, 3,5-dinitrobenzoic acid or of 4-methoxybenzoic acid for neomenthol. The separation of isomenthol by the process according to the invention is best carried out through its esters with 4-methoxybenzoic acid or 3,5-dinitrobenzoic acid.

The d,l-isomer mixture can be esterified by any known method, for example in accordance with the description in Beilstein's Handbuch der Organischen Chemie, 4th Edition, Vol. 9 (1926) on page 115 for the preparation of benzoic acid-l-menthyl ester or ibid., Vol. 9 (Suppl. 3) (1970) on page 408 for the preparation of benzoic acid-d-neomenthyl ester.

The process according to the invention can be carried out by initially preparing a saturated solution of the d,l-ester at temperatures below the melting point of the racemate, preferably at temperatures of from 0° to 20°C. Examples of suitable solvents include hydrocarbons, such as light petrol, cleaning spirit, hexane, cyclohexane, or toluene; ethers such as diethyl ether, diisopropyl ether, dioxane or tetrahydrofuran; ketones, such as acetone, methylethyl ketone, diethyl ketone, methylpropyl ketone, methylbutyl ketone, di-n-propyl ketone or methylisopropyl ketone; or alcohols, such as methanol, ethanol, n-propanol, isopropanol, butanol, linear or branched-chain amyl alcohols or hexanols, benzyl alcohol or cyclohexanol and mixtures of the aforementioned solvents. Preferred solvents are petrol, methanol, ethanol or acetone. The saturated solution separated from the sediment is heated by about 2° C., as a result of which any crystal seeds still present disappear, and is divided into two equal parts. The solutions are then adjusted to a slightly supersaturated state in which there is still no spontaneous seed formation, by cooling to about 1° to 3° C. below the saturation temperature. If one batch is then inoculated with crystals of the l-form and the other with crystals of the d-form only that menthyl ester corresponding to the form of the optically active seed crystals crystallizes out of the supersaturated solution. The crystallizates of both batches can be separated from the mother liquor in the usual ways, for example by filtration or by centrifuging. After they have been combined and reheated, the mother liquors are used to dissolve more racemate and the thus resaturated solution may again be used for the process according to the invention.

Separation can of course, also be carried out by inoculating a melt supercooled by about 1 to 3° C. with crystals of l- or d-menthyl ester. In general, however, separation is carried out using a solvent.

The separation of d,l-methyl esters can be carried out either continuously or in batches. For example, continuous separation can be carried out as shown in the accompanying drawing, which is a schematic flow sheet of a suitable apparatus.

A saturated solution of the $d,l$-menthyl ester is prepared in a 500 liter vessel 1 equipped with a stirring mechanism and cooling coils 2. This solution is filtered off under suction of two metering pumps 4 and 5 through a wire basket 3 which retains most of the solids. Both pumps are adjusted to have the same output and force the streams of solution through candle filters 6 and 7, which separate off any crystals still present, and into a heat exchanger 8, in which the solutions are heated by about 2° C. The solutions are now slightly undersaturated, so that any crystal seeds still present after passage through the filters disappear. In a second heat exchanger 9, the two streams of solution are cooled to about 1° to 3° C. below the saturation temperature and then flow into two 250 liter capacity vessels 11 and 12 which are equipped with stirring mechanisms and cooling coils 10 and 13 and which are at substantially the same temperature as the inflowing solutions. The $l$- or $d$-form is selectively crystallized from the supersaturated solutions in these vessels by addition of seed crystals of the optically pure $l$- or $d$-menthyl esters. The solutions are filtered off from the crystallizing vessels 11 and 12 under suction of two metering pumps 16 and 17, which are adjusted to have the same output, through wire baskets 14 and 15 which retain the crystals. The output of the metering pumps 16 and 17 is lower than that of the pumps 4 and 5 by such an extent that the solution volume in the crystallizing vessels increases at the same rate as the quantity of suspended crystals and the concentration of the solution is thus maintained constant. The streams flowing out of the metering pumps 16 and 17 are combined, restored to the temperature of the dissolution vessel 1 in a heat exchanger 18 and returned to the dissolution vessel, in which they are resaturated with the $d,l$-menthyl ester which is present as sediment and which is continuously or periodically replenished. Crystal suspension is removed from the bottom of the crystallizing vessels 11 and 12 by means of the measuring vessels 19 and 20 or continuously by means of slurry pumps and the crystals separated off, for example by centrifuging. The mother liquors are also returned to the dissolution vessel 1 after having been combined and heated to the temperature of that vessel. The crystallizates of $l$- and $d$-menthol ester obtained by a continuous process or a batch process according to the invention and the $l$- and $d$-menthol obtained from them by hydrolysis are optically pure.

It must be regarded as extremely surprising that optically pure $d$- and $l$-isomers can be obtained by the process according to the invention because, $d,l$-menthol for example cannot be separated into its optical isomers by selective crystallization despite the use of a variety of different solvents and a variety of different working temperatures and concentrations. Thus certain carboxylic acid esters of $d,l$-menthol, especially those of benzoic acid and derivates thereof, had not been expected to lend themselves to separation by selective crystallization.

The invention is further described in the following illustrative examples wherein all parts are by weight unless otherwise expressed.

EXAMPLE 1

220 liters of petrol are cooled to +3°C in a vessel equipped with stirring mechanism and cooling coils. Solid $d,l$-methyl benzoate is added with stirring in a sufficient quantity (about 350kg) to leave behind a small undissolved residue. The solution thus saturated at +3°C is filtered off from the undissolved menthylbenzoate and heated to approximately +5° C. so that any crystal seeds still present disappear. The solution is then introduced in equal parts into two vessels which are equipped with stirring mechanisms and cooling coils, and cooled to 0° C. One of the two containers is inoculated with approximately 5 kg of $l$-menthyl-benzoate crystals and the other with an equivalent quantity of $d$-menthylbenzoate crystals. Crystallization is complete after 1 hour stirring. The crystals are separated from the mother liquor by centrifuging and washed with cold petrol. Approximately 19 kg of each of $d$- and $l$-menthylbenzoate crystals are thus obtained. 5 kg batches of each are retained for inoculating the next batch. Optically pure $d$- and $l$-menthol is obtained from the main quantity by hydrolysis. The mother liquors from both crystallizations are combined and returned together with 28 kg of additional solid menthylbenzoate to the dissolution vessel in which they are resaturated at 3° C.

EXAMPLE 2

A continuous separation process which can be carried out in the apparatus shown in the drawing will now be described. A 500 liter vessel 1 equipped with stirring mechanism and cooling coils 2 contains a solution saturated at +3° C. of $d,l$-menthylbenzoate in petrol and an excess of solid $d,l$-methylbenzoate which is continuously or periodically replenished so that the solution always remain saturated. The solution is filtered off under suction by two metering pumps 4 and 5 through a wire basket 3 which retains most of the solids. Both the metering pumps are adjusted to have the same output of 250 liters per hour and force the respective solutions through candle filters 6 and 7, in which crystal seeds are filtered off, and into a heat exchanger 8, in which the streams are heated from +3° C. to +5° C. so that any crystal seeds which may have passed through the filter are dissolved into the now undersaturated solution. In a second heat exchanger 9, the two streams of solution are cooled to 0° C. and flow at this temperature into two 250 liter capacity vessels 11 and 12 which are equipped with stirring mechanisms, kept at 0° C. by cooling coils 10 and 13 and contain seed crystals of $l$-menthylbenzoate and $d$-menthylbenzoate, respectively. The quantity of seed crystals should be fairly high to enable crystallization to take place as quickly as possible (approximately 200 to 300 g/liter of solvent volume). Two metering pumps 16 and 17 remove the solutions under suction from these crystallizing vessels through wire baskets 14 and 15 which retain the crystals. The metering pumps 16 and 17 are adjusted to a lower output (approximately 190 liters per hour) than the metering pumps 4 and 5 so that the solution volume in both crystallizing vessels increases at the same rate as the quantity of suspended crystals and their quantity per liter thus remains constant. The streams flowing out of the metering pumps 16 and 17 are combined, reheated at +3° C. in a heat exchanger 18 and flow back into the dissolution vessel 1 where they are resaturated with $d,l$-methylbenzoate. At approximately hourly intervals, crystal suspension is removed from the crystallizing vessels in quantities of 60 liters 11 and 12 by means of the 60 liter capacity measuring vessels 19 and 20, and the crystals separated off from the mother liquor, for example by centrifuging. The mother liquors flow back into the dissolution vessel 1 after being heated to +3° C. in the heat exchanger 18. The crystalline esters thus obtained are washed with cold petrol. Approximately 15 kg each of d- and l-menthylbenzoate are obtained per hour. Removal of the crystal suspension from the crystallizing vessels 11 and 12 can also be carried out continuously, for example by means of slurry pumps. Optically pure d- and l-menthol can be obtained by hydrolyzing the d- and l-menthyl esters.

EXAMPLE 3

Two 100 kg batches of d,l-menthylbenzoate are fused by heating to 30° C. in two containers, which are equipped with stirring mechanisms, and subsequently cooled to 25° C. 5 kg of d-menthylbenzoate crystals and 5 kg of l-menthylbenzoate crystals are stirred into the melts. After stirring for 1 hour, crystals are separated off from the melt by centrifuging and washed with cold methanol. Approximately 6.5 kg each of d- and l-menthylbenzoate crystals are obtained in this way and optically pure d- and l-menthol is obtained therefrom by hydrolysis. The melt centrifuged off from the l-menthylbenzoate crystals contains an excess of d-menthylbenzoate (and vice versa). Accordingly, it is advisable, in continuing the process, to heat this melt to 30° C., replace the quantity which has crystallized out with fresh menthylbenzoate, and inoculate with d-menthylbenzoate crystals (the reverse procedure being adopted for the other melt).

EXAMPLE 4

300 liters of petrol are cooled to +10° C. in a vessel which is equipped with a stirring mechanism and cooling coils. Solid d,l-menthylhexahydrobenzoate is added with stirring in sufficiently large quantity (approximately 520 kg) to leave behind a small undissolved residue. The solution thus saturated at +10° C. is filtered off and heated to approximately 12° C. so that any crystal seeds still present are dissolved. The solution is then introduced into another vessel equipped with a stirring mechanism and with cooling coils. After the solution has been cooled to 9° C., it is inoculated with 5 kg of l-menthylhexahydrobenzoate. Crystallization is complete after stirring for about 2 hours and the crystals are separated off from the mother liquor by centrifuging and washed with cold petrol. After drying, approximately 22 kg are obtained, of which 5 kg are retained for inoculating the next batch. The temperature of the mother liquor is adjusted to 9° C. in another vessel equipped with stirring mechanism and similarly crystallized by inoculation with 5 kg of d-menthylhexahydrobenzoate. The optically pure d- and l-menthol is subsequently recovered from the crystallizates obtained by hydrolyzing the d- and l-menthyl esters. The mother liquor is resaturated with d,l-menthylhexahydrobenzoate at 10° C. and the process repeated.

EXAMPLE 5

Two 87 kg batches of d,l-menthyl-4-menthylbenzoate (an oily liquid which is almost impossible to crystallize) are each mixed with 13 kg of methanol in two vessels which are equipped with stirring mechanisms and cooled to −7° C. One of the vessels is inoculated with 5 kg of d-menthyl-4-methylbenzoate and the other with 5 kg of l-menthyl-4-methylbenzoate. After stirring for 1 hour, the crystals obtained are separated off from the mother liquor by centrifuging and washed with cold methanol to yield approximately 7 kg of d- and l-ester. Optically pure d- and l-menthol is obtained by hydrolyzing the d- and l-menthyl esters, respectively.

EXAMPLE 6

Two 80 kg batches of d,l-menthyl-4-ethoxybenzoate are dissolved in 120 kg of toluene in two vessels which are equipped with stirring mechanisms and the solutions cooled to −2° C. One of these vessels is inoculated with 5 kg of d-menthyl-4-ethoxybenzoate crystals and the other with 5 kg of l-menthyl-4-ethoxybenzoate crystals. After stirring for 1.5 hours, the crystals are separated off from the mother liquor by centrifuging. Washing with cold methanol gives approximately 7.0 kg each of d-and l-menthyl-4-ethoxybenzoate which are hydrolyzed into optically pure d- and l-menthol.

EXAMPLE 7

Two 21.4 kg batches of d,l-menthyl-3,5-dinitrobenzoate are dissolved in 178.6 kg of acetone at 25° C. in two vessels which are equipped with stirring mechanisms and the solutions cooled to 15° C. One of the vessels is then inoculated with 5 kg of d-menthyl-3,5-dinitribenzoate crystals and the other with 5 kg of l-menthyl-3,5-dinitrobenzoate crystals. After stirring for 1.5 hours, the crystals are separated off from the mother liquor by centrifuging and washed with cold methanol, to give approximately 7.0 kg of d-menthyl- and 7.0 kg of l-menthyl-3,5-dinitrobenzoate which are hydrolyzed into optically pure d- and l-menthol.

EXAMPLE 8

50 parts by weight of d,l-neomenthyl-4-methylbenzoate are dissolved in 50 parts by weight of acetone in a vessel equipped with stirring mechanism and a cooling system, and cooled to 14.7° C. The solution is inoculated with 2.5 parts by weight of d-neomenthyl-4-methylbenzoate. It is then cooled to 13.8° C. and stirred for a further 20 minutes. The crystals are then separated off from the mother liquor by centrifuging. Washing with cold methanol gives approximately 7.5 parts by weight of d-neomenthyl-4-methylbenzoate. Optically pure d-neomenthol is obtained by hydrolyzing the ester. Optically pure l-neomenthol is similarly obtained by inoculating the mother liquor with l-neomenthyl-4-methylbenzoate.

EXAMPLE 9

80.2 kg of an almost saturated solution consisting of 13 parts by weight of d,l-neomenthyl-4-methoxybenzoate and 87 parts by weight of methanol, are cooled to +2.5° C. in a vessel which is equipped with stirring mechanism and a cooling system, and 300 g of d-neomenthyl-4-methoxybenzoate are then added.

The mixture is stirred for approximately 50 minutes during which its temperature is reduced to −3.5° C. The crystals which accumulate are filtered off under suction to give 1.23 kg of d-neomenthyl-4-methoxybenzoate. Optically pure d-neomenthol is obtained by hydrolyzing the ester.

l-neomenthol can be similarly obtained by adding l-neomenthyl-4-methoxybenzoate to the d,l-neomenthyl-4-methoxybenzoate solution and by hydrolyzing the obtained ester.

EXAMPLE 10

5 g of d,l-neomenthyl-3,5-dinitrobenzoate are dissolved in 33 g of acetone in a vessel which is equipped with stirring mechanism and a cooling system and 0.5 g of d-neomenthyl-3,5-dinitrobenzoate are then added. The solution is then cooled to 16.9° C. and stirred for 30 minutes. The crystals formed are filtered off under suction, to give 1.145 g of d-neomenthyl-3,5-dinitrobenzoate. l-neomenthol-3,5-dinitrobenzoate is similarly obtained by adding 0.5 g of l-neomenthyl-3,5-dinitrobenzoate to the solution.

Optically pure d- and l-neomenthol are obtained by hydrolyzing the corresponding ester.

EXAMPLE 11

31 parts by weight of an almost saturated solution consisting of 78.4 percent by weight of d,l-isomenthyl-4-methoxybenzoate and 26 percent by weight of methanol, are heated to +50° C. in a vessel which is equipped with stirring mechanism and 0.05 part by weight of d-isomenthyl-4-methoxybenzoate are then added.

The mixture is stirred for approximately 60 minutes during which its temperature is reduced to +45° C. The crystals which accumulate are filtered off under suction. Washing with cold methanol gives 0.65 part by weight of d-isomenthyl-4-methoxybenzoate. Optically pure d-isomenthol is obtained by hydrolyzing the ester.

Optically pure l-isomenthol is similarly obtained by inoculating the mother liquor with l-isomenthyl-4-methoxybenzoate.

It will be appreciated that the instant specification and examples are set forth by way of illustration and not limitation, and that various modifications and changes may be made without departing from the spirit and scope of the present invention.

EXAMPLE 12

43.5 g of d,l-isomenthyl-3,5-dinitrobenzoate are dissolved in 6.5 g of hot toluene in a heatable vessel which is equipped with stirring mechanism and reflux condenser. The solution is heated to +105° C. and then inoculated with 0.5 g of d-isomenthyl-3,5-dinitrobenzoate. The mixture is stirred for approximately 30 minutes during which its temperature is reduced to 103° C. The crystals formed are filtered off under suction, to give 5.6 g d-isomenthyl-3,5-dinitrobenzoate. Optically pure d-isomenthyl is obtained by hydrolyzing the ester.

Optically pure l-isomenthol is similarly obtained by inoculating the mother liquor resp. the initial solution with l-isomenthyl-3,5-dinitrobenzoate.

EXAMPLE 13

55 g of d,l-neomenthylbenzoate are dissolved in 45 g of methanol in a vessel equipped with stirring mechanism and a cooling system, and cooled to −13.5° C. The solution is inoculated with 0.6 g d-neomenthylbenzoate. It is then cooled to −14° C. and stirred for a further 35 minutes. The crystals which accumulate are filtered off under suction to give 5.6 g d-neomenthylbenzoate. Optically pure d-neomenthol is obtained by hydrolyzing the ester.

Optically pure l-neomenthol is similarly obtained by inoculating the mother liquor resp. to initial solution with l-neomenthylbenzoate followed by hydrolysis.

EXAMPLE 14

31 g of d,l-neomenthylhexahydrobenzoate are dissolved in 69 g of methanol in a vessel equipped with stirring mechanism and a cooling system, and cooled to +14° C. The solution is inoculated with 0.35 g d-neomenthylhexahydrobenzoate. It is then cooled to +13° C. and stirred for a further 25 minutes. The crystals which accumulate are filtered off under suction to give 2.9 g d-neomenthylhexahydrobenzoate. Optically pure d-neomenthol is obtained by hydrolyzing the ester.

Optically pure l-neomenthol is similarly obtained by inoculating the mother liquor resp. the initial solution with l-neomenthylhexahydrobenzoate followed by hydrolyzis.

What is claimed is:

1. A process for the separation of optically active d- and l-isomers of a compound selected from the group consisting of menthol, neomenthol and isomenthol, which comprises forming a super-saturated solution or a supercooled melt consisting essentially of a d,l-isomeric mixture of an ester of the compound with an acid selected from the group consisting of benzoic acid, hexahydrobenzoic acid and benzoic acid substituted by up to 2 lower alkyl or alkoxy, fluorine, chlorine, bromine or nitro groups inoculating the solution or melt with crystals of the d- or l-form of the ester to effect selective crystallization of one of the two optical isomers; separating the crystals and subjecting them to hydrolysis to yield the corresponding enantiomorph of the starting compound.

2. A process as claimed in claim 1, wherein the acid is benzoic acid, hexahydrobenzoic acid, 4-methylbenzoic acid, 3,5-dinitrobenzoic acid, 4-methoxybenzoic acid or 4-ethoxybenzoic acid.

3. The process of claim 1, wherein the compound is menthol and the acid is benzoic acid, hexahydrobenzoic acid, 4-methylbenzoic acid, 3,5-dinitrobenzoic acid or 4-ethoxybenzoic acid.

4. The process of claim 1, wherein the compound is neomenthol and the acid is 4-methylbenzoic acid, 3,5-dinitrobenzoic acid or 4-methoxybenzoic acid.

5. The process of claim 1, wherein the compound is isomenthol and the acid of 4-methoxybenzoic acid or 3,5-dinitrobenzoic acid.

* * * * *